United States Patent [19]

Katoh et al.

[11] Patent Number: 5,308,468
[45] Date of Patent: May 3, 1994

[54] ION SENSOR

[75] Inventors: Takashi Katoh; Jun-ichi Tokumoto, both of Nagoya, Japan

[73] Assignee: NGK Spark Plug Co., Ltd., Aichi, Japan

[21] Appl. No.: 10,479

[22] Filed: Jan. 28, 1993

Related U.S. Application Data

[63] Continuation of Ser. No. 699,386, May 14, 1991, abandoned.

[30] Foreign Application Priority Data

May 14, 1990 [JP] Japan ................. 2-121138

[51] Int. Cl.$^5$ ............................. G01N 27/26
[52] U.S. Cl. ....................... 204/419; 204/416; 204/418; 204/433; 204/435
[58] Field of Search ............... 204/416, 418, 419, 433, 204/435

[56] References Cited

U.S. PATENT DOCUMENTS

| | | | |
|---|---|---|---|
| 4,214,968 | 7/1980 | Battaglia et al. | 204/416 |
| 4,358,516 | 11/1982 | Lange | 204/416 |
| 4,454,007 | 6/1984 | Pace | 204/416 |
| 4,508,613 | 4/1985 | Busta et al. | 204/419 |
| 4,686,012 | 8/1987 | Engell et al. | 204/419 |

FOREIGN PATENT DOCUMENTS

| | | |
|---|---|---|
| 56-5687 | of 0000 | Japan . |
| 57-161544 | of 0000 | Japan . |
| 57-196146 | of 0000 | Japan . |
| 1-262459 | of 0000 | Japan . |
| 59-502154 | of 0000 | Japan . |

OTHER PUBLICATIONS

Solid Electrolytes, Hagenmuller and Gool, Academic Press 1978, pp. 406–407.

*Primary Examiner*—John Niebling
*Assistant Examiner*—Bruce F. Bell
*Attorney, Agent, or Firm*—Fish & Richardson

[57] ABSTRACT

Ion sensor having an ion-selective electrode and a reference electrode, both being unified, without internal liquid solution. The ion-selective electrode part has a solid solution of halogenide of conducting ions of solid electrolyte and halogenide of metal for an internal electrode, e.g., NaCl-AgCl solid solution. The reference electrode part has a solid solution of halogenide of the group Ia or IIa, e.g., Na, K, and a halogenide of metal for an internal electrode, e.g., NaCl-AgCl solid solution. The electrode parts are supported by an insulating substrate. A solid electrolyte such as NASICON or ionophore such as valinomycin is used as an ion-sensitive membrane.

12 Claims, 3 Drawing Sheets

LIQUID TO BE MEASURED

RESPONSE OF Na-ION SENSOR

RESPONSE OF K-ION SENSOR

ION SENSOR

This is a continuation of application Ser. No. 07/699,386, filed May 14, 1991, now abandoned.

TECHNICAL FIELD

This invention relates to an ion sensor utilized for therapeutic measurement (clinical examination), water quality inspection or process control in foodstuff industry or in chemical engineering.

BACKGROUND OF THE INVENTION

An ionic electrode method, which makes use of an ion-selective electrode, has been known for detecting ions in a sample solution. By the ion-selective electrode herein is meant such electrode which detect the potential difference corresponding to the activities of anions and cations contained in the solution that is the thermodynamically compensated concentrations of the anions and cations, and which is provided with a membrane of an ion-sensitive material selectively sensitive to certain predetermined ion species.

However, with the ionic electrode method, it is necessary to use an ion-selective electrode and a reference electrode separately. Also, in many cases, an internal liquid solution is employed for each of the electrodes. As a result, the electrodes tend to be increased in size and, in addition, the sample being measured needs to be used in a larger quantity. If the internal liquid solution is not used and a lead wire is directly attached to the ion-sensitive membrane to take out the electrical potential, the response time tends to be prolonged or fluctuated and hence a stable measurement cannot be achieved. If the internal liquid solution is used, attention must be directed to the state of replenishment or maintenance of the internal liquid solution.

SUMMARY OF THE DISCLOSURE

It is therefore a principal object of the present invention to provide an ion sensor in which the internal liquid solution in the ion-selective electrode and the reference electrode are eliminated to reduce the size of the electrodes, and in which the electrodes are unified in one unit to enable the measurement even with the use of a minor quantity of the sample under measurement.

It is another object of the present invention to provide an ion sensor in which measurement may be made with reduced response output fluctuations and a shortened response time.

It is yet another object of the present invention to provide an ion sensor in which measurement may be made with the least maintenance operations.

In one aspect of the present invention, the ion sensor is provided in which an ion-selective electrode part and a reference electrode part are supported by an insulating substrate, wherein said ion selective electrode part comprises a solid electrolyte ceramic as an ion-sensitive membrane, a solid solution of a halogenide of conducting ions of the solid electrolyte and a halogenide of a metal of an internal electrode, and said internal electrode, in the order as viewed from the side of said ion-selective electrode part to be contacted by ions under measurement, and wherein said reference electrode part comprises a solid solution of a halogenide of a metal of the group Ia or IIa of the International Periodic Table and a halogenide of a metal of an internal electrode, and said internal electrode, in the order as viewed from the side of the reference electrode part to be contacted by ions under measurement.

In another aspect of the present invention, an ionophore as the ion-sensitive membrane is provided in the ion-selective electrode part according to the first aspect so as to be closer to the side contacted by ions that said solid electrolyte ceramic.

If the ion-sensitive membrane of the ion-selective electrode part is the solid electrolyte ceramic, according to the first aspect of the invention, the membrane exhibits ion response conforming to the species of the conducting ions. That is, if the ion-sensitive membrane is a ceramic capable of conducting sodium (Na) ions, a potential corresponding to the Na ion concentration may be obtained. If an ionophore as the ion-sensitive membrane is additionally provided on the surface of the ceramic of the solid electrolyte ceramic, according to the second aspect of the invention, the electrical potentials corresponding to the concentrations of a variety of ions, i.e., cations, such as Na-, K-, Li-, Ca-, $NH_4$- or Mg ions, or anions, such as nitric-, sulfuric- or hydrochloric acid ions, may be obtained.

It will be noted that the solid solution of the halogenides, provided in each of the ion-selective electrode part and the reference electrode part, is effective to stabilize the electrical potential quickly without causing any fluctuations in the electrical potential practically. In addition, since the same one or more halogen species are used for the halogenide of conducting ions or of the metal of the group Ia or IIa and the halogenide of the metal of the internal electrode in each electrode part, the reversible equilibrium state may be realized easily between the conducting ion species of the solid electrolyte ceramic and the metal(s) of the internal electrodes.

Using the sensor of the present invention, the response time (the time until the potential reaches a stationary state) may be shortened. Initial output fluctuations may be minimized because of the excellent response properties of the present sensor. In addition, since the sensor is of the fully solid-state type, it may be reduced in size and the measurement may be made with a small quantity of the sample. Besides, the sensor may be arranged as a multiple type ion sensor provided with several kinds of ion-selective electrodes in a sole sensor unit.

In summary, the ion sensor of the present invention, which is of the fully solid type and in which the ion-selective electrode and the reference electrode are unified into one unit, has the following meritorious effects:

(i) It has a short response time and superior response characteristics with only little response fluctuations;

(ii) it may be reduced in size easily and used with a minor quantity of the sample being measured;

(iii) it may be arranged in various shapes, such as disctubular or needle shape, from which an optimum shape may be selected to suit the type of the measurement to be made and the material to be measured;

(iv) it is highly simplified in maintenance; and (v) it may be used instantaneously for measurement.

In addition, the ion sensor of the present invention (a) may be adapted as a multiple type ion sensor provided with multiple functions, or (b) may be used as an ion sensor capable of detecting various different ions by changing the ionophore-containing high polymeric membrane with another.

BRIEF DESCRIPTION OF THE DRAWINGS

FIGS. 1 and 2 are schematic views showing an ion sensor according to a first embodiment of the present invention, wherein FIG. 1 is a plan view and FIG. 2 a cross-sectional view thereof;

FIGS. 4 and 5 are schematic views showing illustrative methods for measuring the ion concentration by the ion sensor of the present invention, wherein FIG. 4 shows a method in which the solution to be measured is dripped on the sensor and FIG. 5 a method in which the sensor is immersed in a solution to be measured; and FIGS. 6 and 7 are charts showing changes in the potential against the ion concentration as measured in measurement tests employing the ion sensors of the embodiments 1 and 2, wherein FIG. 6 is such chart for the Embodiment 1 (Na ion sensor) and FIG. 7 is such chart for the Embodiment 2 (K ion sensor).

DESCRIPTION OF THE PREFERRED EMBODIMENTS

Figure 1:
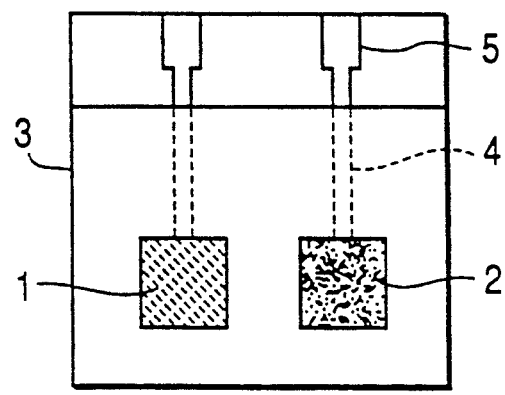

For achieving a stable electrical potential, the solid solution of the halogenides provided in the ion-selective electrode part is the solid solution of a halogenide of conducting ions of the solid electrolyte ceramic and a halogenide of a metal of the internal electrode. Meanwhile, in order that the state of reversible equilibrium between the conducting ions and the metal of the internal electrode may be reached more readily, the same species of the halogens in the solid solution are used for the halogenide of conducting ions and of the metal of the internal electrode. For example, when the conducting ions are Na ions and the metal of the internal electrode is Ag, it is preferred to use solid solution of NaF-AgF, NaCl-AgCl, NaBr-AgBr or NaI-AgI.

On the other hand, the solid solution of the halogenide provided in the reference electrode part is the solid solution of a halogenide of a metal of the group Ia or IIa of the International Periodic Table and a halogenide of a metal of the internal electrode part. As in the solid solution in the ion-selective electrode part, the same halogen species are used for each halogenide in the solid solution of the reference electrode part. Although the most stable electrical potential and excellent response characteristics may be obtained with the use of Na or K as the metal of the group Ia or IIa, Li or Ca etc. may also be used, depending on the ion species to be measured. Since the reference electrode shows a constant potential independently of the concentrations of the ions to be measured, the solid solution of K halogenide may be used even when Na ions are measured. Also, when the ions to be measured are other than Na, it is preferred to use halogenides of Na or K in view of stability and response characteristics. For this reason, if the metal of the internal electrode is Ag, solid solution of NaF- AgF, NaCl-AgCl, NaBr-AgBr, NaI-AgI, KF-AgF, KCl- AgCl, KBr- AgBr or KI-AgI is advantageously employed.

Although the solid solution of the halogenides of the ion-selective electrode part and the solid solution of the halogenides of the reference electrode part are preferably of the same composition, they may also be of different compositions.

In general, the solid electrolyte ceramic exhibits an ion response proper to its conducting ion species. According to the present invention, it is preferred to use the solid electrolyte ceramic which will provide a dense membrane and remain stable in the solution to be measured. Above all, Na-conducting ceramics, such as, for example, Na-$\beta$- alumina, Na-$\beta''$-alumina or NASICON represented by the formula $Na_{1+x} Zr_2 Si_x P_{3-x} O_{12}$ ($0 \leq x \leq 3$), are most preferred. Meanwhile, the solid electrolyte ceramic has a relative density preferably of 95 percent or higher, more preferably of 99 percent or higher, and a mean crystal grain size preferably of 10 $\mu$m or less and more preferably of 5 $\mu$m or less.

If an ionophore (ionic carrier) is additionally provided on the surface of the solid electrolyte ceramic, any of the ionophores commonly used in the art may be employed. For example, natural substances, above all, physiologically active materials, such as valinomycin, monensin, rhodopsin, nonactin or monactin; or synthetic materials, such as crown ether (a set of macrocyclic polyethers), or noncyclic nonylphenoxy polyethanol etc., may be used, either alone or as a mixture. The ionophore may be supported in a dispersed state on polymeric membranes, such as membranes of poly (vinyl chloride) (PVC), poly (vinyl acetate) or silicone rubber, in the usual manner, or supported on a surface of the solid electrolyte ceramic, which has been rendered porous to a larger extent.

Since the ionophores are ion-selective to determine responsive ions, it is unnecessary to select the solid electrolyte ceramic which will specifically conduct the ions to be measured.

As the internal electrode, the electrode of such materials as Ag, Au, Pt or amalgam, may be employed. However, the Ag electrode is most preferred, because amalgam is unsatisfactory in operational safety, while Au and Pt are unsatisfactory in both the costs and operational stability.

The various components of the ion-selective electrode part and the reference electrode part (e.g., solid electrolyte ceramics except the ionophore), are preferably present in the melt-adhesion state, so as not to inhibit the response properties of the sensor. Turning to the thicknesses, it is preferred that the thicknesses of the solid solution of the halogenides, the solid electrolyte ceramic, the ionophore and the internal electrode be 50 $\mu$m to 2 mm, 50 $\mu$m to 2 mm, 1 $\mu$m to 500 $\mu$m and not less than about 10 $\mu$m, respectively.

Figure 2:
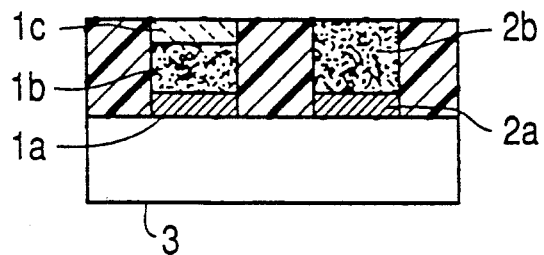
Figure 3:
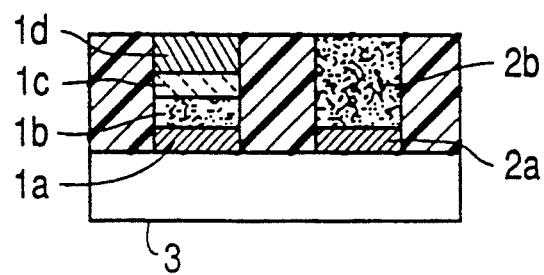
FIG. 3 is a schematic cross-sectional view showing an ion sensor according to a second embodiment of the present invention.

It will be noted that the ion-selective electrode part and the reference electrode part are encapsulated in an insulating substrate, such as ceramic, resin or the like high polymeric material, as shown in FIGS. 1 to 3. In this manner, the sensor may be reduced in size as compared to the conventional sensor in which the ion-selective electrode and the reference electrode are provided separately, so that measurement becomes possible with the use of the sample of a small quantity.

The ion sensor of the present invention may be extensively applied to measurement of the concentrations, that is, measurement of the activities, of a wide variety of ions besides $Na^+$ and $K^+$. Thus it may be applied to any cations, and also to anions, such as nitric, sulfuric or hydrochloric acid ions.

Figure 4:
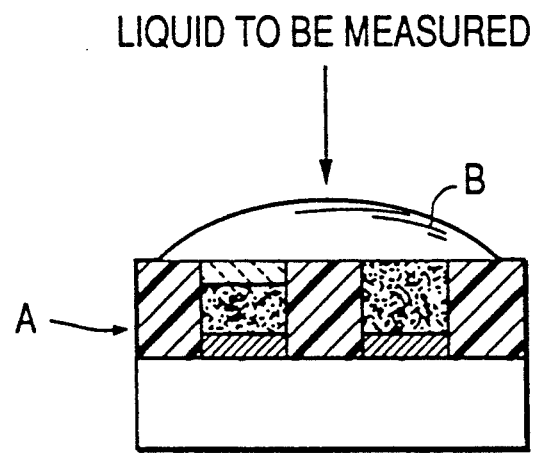
Figure 5:
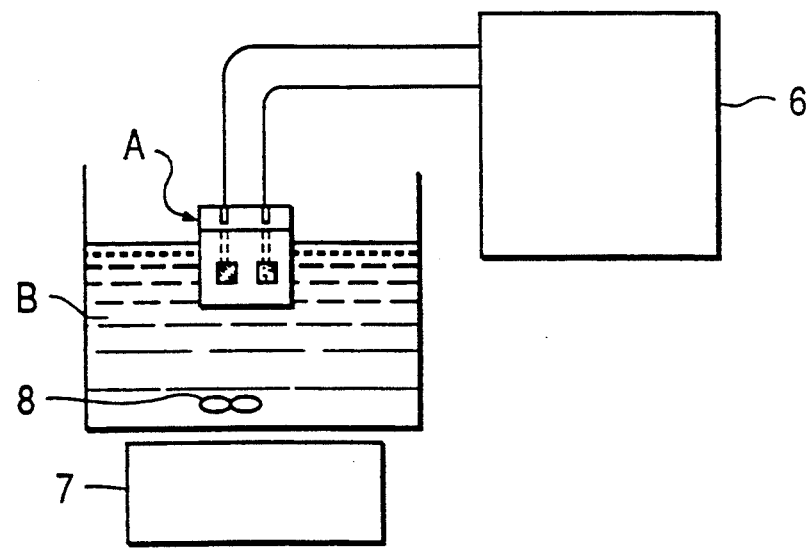

In measurement, the sensor may be immersed in a solution to be measured (FIG. 5). Alternately, the solution to be measured may be dripped onto the sensor so that the ion-selective electrode part and the reference electrode part may simultaneously be brought into contact with the solution under measurement (FIG. 4).

EXAMPLES

Example 1

(i) A disc-shaped plate of sintered NASICON (general formula, $Na_3 Zr_2 Si_2 PO_{12}$) with a diameter of 5 mm and a thickness of 0.5 mm was provided by sintering at about 1200° C., (ii) NaCl and AgCl were mixed thoroughly at a molar ratio of 1:1 and the resulting mixture was press-molded to a disc-like pellet having a diameter of 5 mm and a thickness of 1 mm.

(iii) The pellet (ii) and the NASICON disc (i) were stacked on one of two silver electrodes, while only the pellet (ii) was stacked on the other silver electrodes, to provide stacked units. The two silver electrodes had been previously metallized on an alumina insulating substrate.

(iv) The stacked units from (iii) were heat-treated at 600° C. for 30 minutes to form an NaCl-AgCl solid solution and to fuse the stacked units to the silver electrodes in the order.

(v) The fused units, respectively, are sealed by epoxy resin, except a part of the uppermost surfaces of the NASICON disc of the ion electrode and the solid solution of the reference electrode.

In this manner, a sodium ion sensor substantially as shown in schematic FIGS. 1 and 2 has been completed provided that the silver electrodes prepared had a round shape of 5 mm in diameter and were disposed at an interval of 2 mm between the both. Also the heights of the stacked units on both the electrodes were different from each other, i.e., different from FIG. 2. Note that the embodiment just like FIG. 2 is possible, e.g., by modifying the thickness of the NaCl-AgCl pellet to 1.5 mm.

Example 2

1 part by weight of valinomycin, 17 parts by weight of polyvinyl chloride and 82 parts by weight of dioctyl adipate were dissolved in tetrahydrofuran. The resulting solution was dripped on the ion-selective electrode part of a sensor prepared in the same way as in Example 1, and was subsequently dried. In this manner, a potassium ion sensor, in which the ion selective electrode part is coated by a polymeric membrane containing the ionophore, i.e. valinomycin, as shown in FIG. 3, was prepared.

Figure 6:
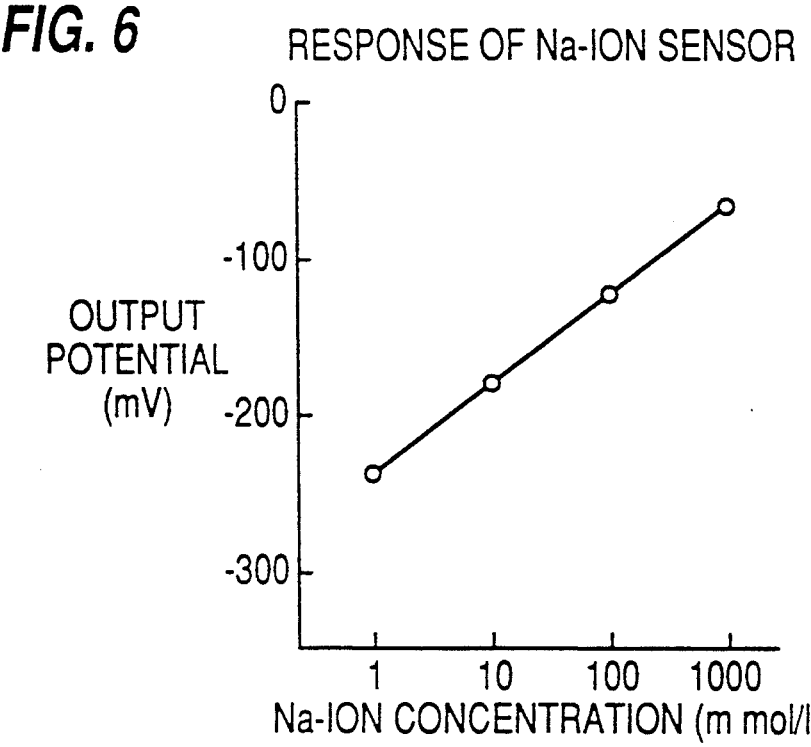
Figure 7:
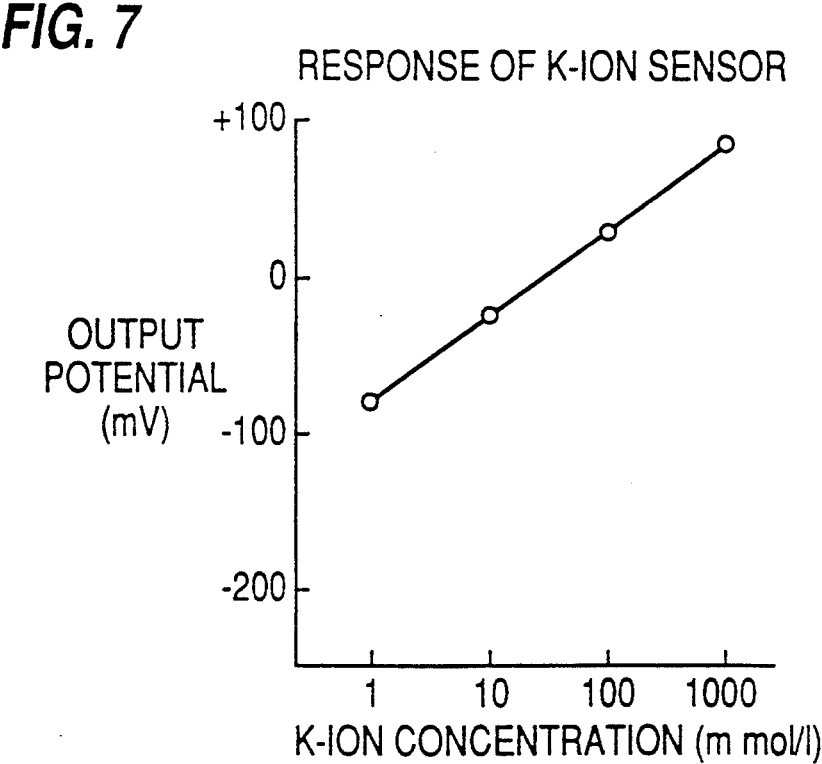

Using the ion sensors of the Examples 1 and 2, potentiometric measurement was conducted to check for response of the sensors to Na and K ions e.g., as shown in FIG. 4 in which one droplet of a solution to be measured from a pippet (about 50 $\mu l$) was applied. Linear response conforming to the Nernstian equation could be obtained in the range of concentration from 1 to 1,000 mmol/l with each of the ion sensors, as shown in FIGS. 6 and 7. As to the response time, the response has also become constant within 10 seconds. Fluctuations in the calibration curves, obtained with three sensors each for the Na and K ions, could be hardly noticed. Meanwhile, in Example 2, response to $K^+$ ions of valinomycin (ionophore) was not obstructed by $Na^+$-conducting NASICON (the solid electrolyte ceramic).

In FIGS. 1 to 3, 1 denotes an ion-selective electrode part (formed by an internal Ag electrode 1a, a solid solution of halogenides 1b and a solid electrolyte ceramic 1c); 2 a reference electrode part (formed by an internal electrode 2a and a solid solution of halogenides 2b); 3 an insulating substrate; 4 lead wires; and 5 lead terminals. In FIG. 4, A denotes an ion sensor, B a solution to be measured, 6 an electrometer, 7 a magnetic stirrer and 8 an agitator.

The above describe sensor may be formed as a tubular or needle-shaped sensor, besides the flat disc-shaped sensor employing the above mentioned substrate. The ion sensor of the present invention may also be arranged as a multiple ion sensor in which a large number of electrodes, each formed by a membrane of the solid electrolyte ceramic, are encapsulated in an insulating substrate of the sensor and in which different ionophores are associated with the electrodes. In this case, the solid electrolyte ceramic of a sole and the same kind may be used, provided that the different ionophores are used for the respective electrodes. The diameter of electrodes and the pellets stacked thereon can be further reduced to a size ranging from 1 mm to 0.5 mm or less in diameter, the shape being either round, square etc. The interval becomes narrower correspondingly. The surface extending over the ion-selective electrode part and the reference electrode part may be curved (convex or concave) or bent by certain angle. Further, if resin or like insulating substrate having not sufficient heat resistance as compared to the heating temperature necessary to fuse the stacked pellet to form stacked units, the substrate may be applied after preparation of the stacked units.

It should be noted that modifications in the art may be done without departing from the gist and scope of the present invention as disclosed herein and claimed hereinbelow.

What is claimed is:

1. An ion sensor comprising in a single unit, an ion selective electrode and a reference electrode, each electrode being supported by an insulating substrate, wherein said ion-selective electrode comprises, respectively, a solid electrolyte ceramic as an ion-sensitive membrane, a solid solution mixture of a halogenide of conducting ions of the solid electrolyte, and a halogenide of a metal of an internal electrode, and an internal electrode, in top to bottom order as viewed from the side of said ion-selective electrode to be contacted by ions under measurement, and wherein said reference electrode comprises, respectively, a solid solution mixture of a halogenide of a metal of the group Ia or IIa of the International Periodic Table, and a halogenide of a metal of an internal electrode, and an internal electrode, in top to bottom order as viewed from the side of the reference electrode part to be contacted by ions under measurement.

2. An ion sensor comprising in a single unit, an ion selective electrode and a reference electrode, each electrode being supported by an insulating substrate, wherein said ion-selective electrode comprises, respectively, an ionophore as an ion-sensitive membrane, a solid electrolyte ceramic, a solid solution mixture of a halogenide of conducting ions of the solid electrolyte, and a halogenide of a metal of an internal electrode, and an internal electrode, in top to bottom order as viewed from the side of said ion-selective electrode to be contacted by ions under measurement, and wherein said reference electrode comprises, respectively, a solid solution mixture of a halogenide of a metal of the group Ia or IIa of the International Periodic Table, and a halogenide of a metal of an internal electrode, and an internal electrode, in top to bottom order as viewed from the side of the reference electrode part to be contacted by ions under measurement.

3. An ion sensor as set forth in claim 1 or 2, wherein the halogenide of conducting ion of the solid electrolyte and the halogenide of the metal of the internal electrode are of the same halogen species for said solid solution in the ion-selective electrode part.

4. An ion sensor as set forth in claim 3, wherein the solid solution is selected from the group consisting of NaF-AgF, NaCl-AgCl, NaBr-AgBr and NaI-AgI.

5. An ion sensor as set forth in claim 1 or 2, wherein the halogenides of the metal of the group Ia or IIa and of the metal of the internal electrode are of the same halogen species for said solid solution in the reference electrode part.

6. An ion sensor as set forth in claim 1 or 2, wherein the metal of the group Ia or IIa of the Periodic Table in the reference electrode part is Na or K.

7. An ion sensor as set forth in claim 5, wherein the solid solution is selected from the group consisting of NaF-AgF, NaCl-AgCl, NaBr-AgBr, NaI-AgI, KF-AgF, KCl-AgCl, KBr-AgBr and KI-AgI.

8. An ion sensor as set forth in claim 1 or 2, wherein the solid solution in the ion-selective electrode part and the solid solution in the reference electrode part are of the same composition.

9. An ion sensor as set forth in claim 1 or 2, wherein said solid electrolyte ceramic is selected from the group consisting of Na-$\beta$-alumina, Na-$\beta''$-alumina and NASICON represented by the formula $Na_{1+x} Zr_2 Si_x P_{3-x} O_{12}$ where $0 \leq x \leq 3$.

10. An ion sensor as set forth in claim 1 or 2, wherein components of the ion-selective electrode part and the reference electrode part, except the ionophore, are fused to each other.

11. An ion sensor as set forth in claim 1 or 2, wherein the insulating substrate is selected from the group consisting of ceramic and resin.

12. An ion sensor as set forth in claim 1 or 2, wherein said ion-selective electrode part and said reference electrode part are disposed in close proximity to each other.

* * * * *